(12) United States Patent
Price

(10) Patent No.: US 6,470,736 B2
(45) Date of Patent: Oct. 29, 2002

(54) APPARATUS AND METHOD FOR CAPILLARY VISCOMETRY OF FLUIDS

(75) Inventor: Brian G. Price, Pittsford, NY (US)

(73) Assignee: Eastman Kodak Company, Rochester, NY (US)

(*) Notice: Subject to any disclaimer, the term of this patent is extended or adjusted under 35 U.S.C. 154(b) by 16 days.

(21) Appl. No.: 09/773,290

(22) Filed: Jan. 31, 2001

(65) Prior Publication Data

US 2002/0139175 A1 Oct. 3, 2002

(51) Int. Cl.[7] ............................................. G01N 11/04
(52) U.S. Cl. ..................... 73/54.04; 73/54.01; 73/54.02
(58) Field of Search ............................ 73/54.01, 54.02, 73/54.04, 54.07, 54.16, 54.38

(56) References Cited

U.S. PATENT DOCUMENTS 2,095,282 A * 10/1937 Payne ........................ 73/54.04
3,071,961 A * 1/1963 Heigl et al. ................ 73/54.04
4,495,798 A * 1/1985 Ehrgott ......................... 73/169
4,615,310 A * 10/1986 Umeha et al. ............ 123/90.33

FOREIGN PATENT DOCUMENTS

GB          2233461 A  *  1/1991  ................ 73/54.09

* cited by examiner

Primary Examiner—Daniel S. Larkin
Assistant Examiner—Michael Cygan
(74) Attorney, Agent, or Firm—Clyde E. Bailey, Sr.

(57) ABSTRACT

An apparatus and method for determining viscosity of a low viscous fluid. A narrow tube samples a fluid sample. The apparatus or capillary viscometer determines viscosity within average relative deviation of less than 2% over a range of viscosity greater than two decades by mass flow rate. The apparatus includes a glass capillary viscometer with thermal jacket, balance with serial interface, and software for computer interface.

17 Claims, 2 Drawing Sheets

APPARATUS AND METHOD FOR CAPILLARY VISCOMETRY OF FLUIDS

FIELD OF THE INVENTION

The invention relates generally to the field of fluid flow measurements. More specifically, the invention relates to an apparatus and method of rapidly determining viscosity of a low viscosity fluid, such as an ink jet printing ink formulation.

BACKGROUND OF THE INVENTION

The need for rapid measurement of viscosity of low viscosity fluids has recently arisen in the context of ink jet printing ink formulation where the additional complication of opacity excludes volumetric capillary systems with optical detection. In the development of ink jet printing inks there is the need for expedient viscosity measurement of numerous samples in the range from 1–20 cp. This range is most conveniently accessed by standard capillary methods. Existing devices use time elapsed during efflux of a fixed volume of fluid, typically relying on optical detection of the meniscus of the sample fluid as it passes through the capillary. Since ink jet printing inks are typically opaque and of low surface tension, such devices and methods are inapplicable as very small amounts of residual fluid can obscure the passing of the meniscus. Other devices and methods exist for detecting the meniscus of the fluid, such as thermal conductivity. These devices and methods, however, are known to inflate the price of the fluid measurement process. Hence, their routine use among many laboratory sites would not be cost effective. Additionally, the accuracy provided by such instruments exceeds that which is necessary for many industrial applications.

Therefore, a need persists in the art for an apparatus and method for rapidly measuring the viscosity of low viscosity fluids, such as ink jet printing ink formulations, that is easy to construct and use.

SUMMARY OF THE INVENTION

It is, therefore, an object of the invention to provide an apparatus for rapidly measuring viscosity of a low viscosity fluid.

Another object of the invention is to provide an apparatus for measuring viscosity of fluids having a viscosity in the range from 1 cps to about 20 cps.

Yet another object of the invention is to provide a method of rapidly measuring the viscosity of a fluid by mass flow rate.

The present invention is directed to achieving one or more of the objects, features and advantages set forth herein. Briefly summarized, according to one aspect of the present invention, an apparatus for measuring viscosity of a fluid has a tube for sampling a fluid. The tube has a fluid inlet orifice and a fluid outlet orifice. A fluid sample container is arranged beneath the tube for receiving a fluid sample exiting the fluid outlet orifice of the tube. The fluid sample container is supportedly arranged on a balance that determines weights of the fluid sample container during fluid sampling. A data processing device, such as a computer, operably connected to the balance records and processes sequential weights of the fluid sample container during fluid sampling. The computer incorporates a computer readable program for enabling the computer to receive a plurality of signals representing the sequential weights of the fluid sample container. The computer then determines the viscosity of the fluid sample based on this plurality of signals.

In another aspect of the invention, a method of measuring viscosity of a fluid comprises the step of introducing a fluid sample into an elongated, narrow tube. The temperature of the fluid sample flowing through the elongated tube is maintained and controlled by a temperature barrier layer arranged about the tube. Fluid flowing through the tube passes into a sample container supported on a digital balance that enables a determination of a plurality of weights of the fluid sample. The plurality of weights of the fluid sample is then converted into a measure of viscosity of the fluid sample.

The present invention has numerous advantages over existing developments including: it produces rapid viscosity measurements of low viscosity fluids; and, it is simple to use and cost effective to manufacture.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

DETAILED DESCRIPTION OF THE INVENTION

Figure 1B:
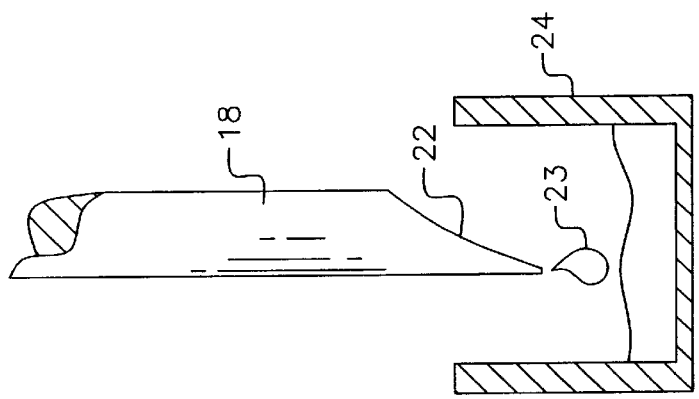
FIG. 1B is an enlarged, partial side view of the drip portion of the tube.
Figure 1A:
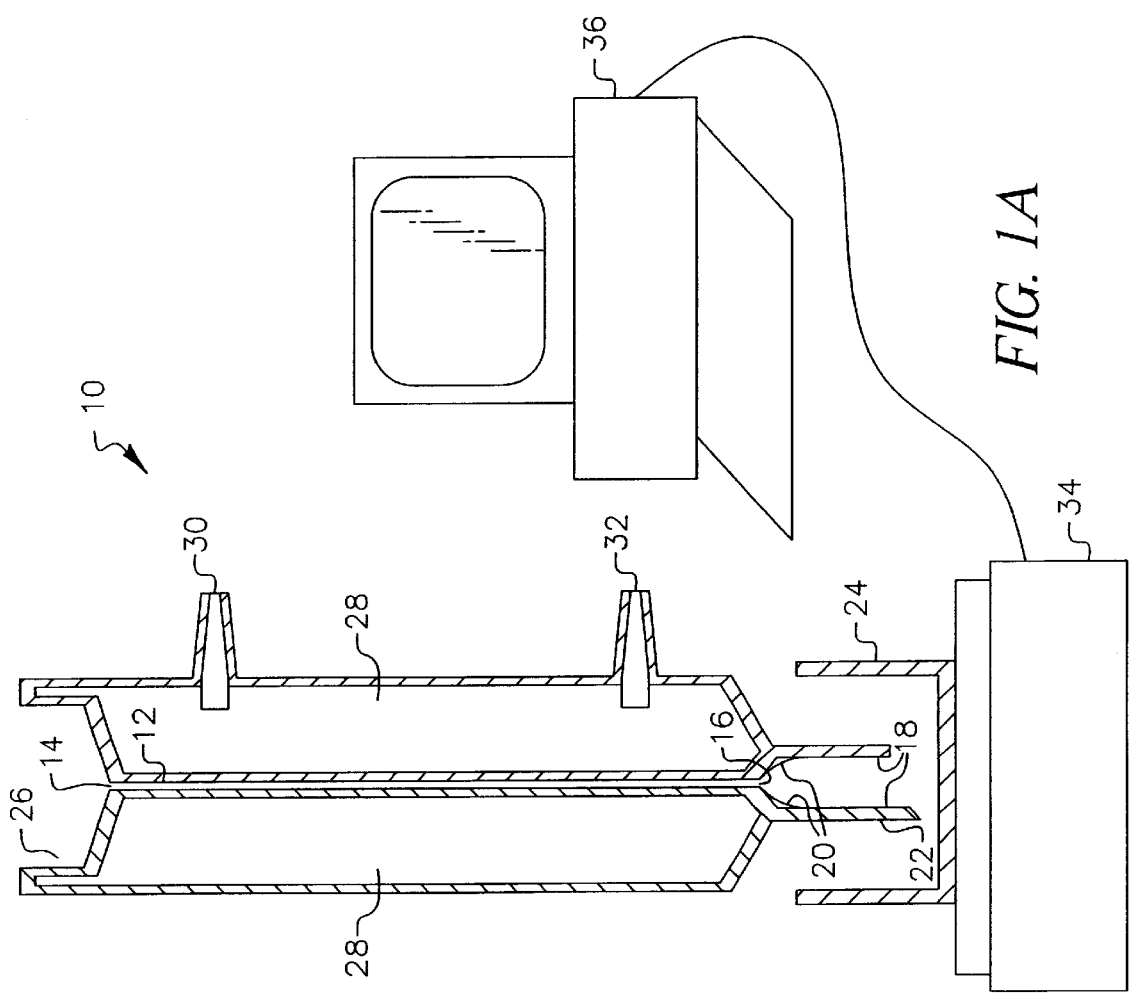
FIG. 1A is a schematic of the apparatus of the invention for measuring viscosity of a fluid.

Turning now to the drawings, and in particular to FIG. 1A, apparatus 10 of the invention for measuring the viscosity of a fluid sample is illustrated. Apparatus 10 is most suitable for low surface tension and opaque fluid formulations, such as those used in ink jet printing inks. Broadly defined, apparatus 10 has an upright standing, elongated narrow tube 12 for sampling a fluid sample. Elongated narrow tube 12, preferably made of either glass or plastic, has a fluid inlet orifice 14 and a fluid outlet orifice 16 opposite the fluid inlet orifice 14. In the preferred embodiment, a drip portion 18 extends downwardly from the fluid outlet orifice 16, as shown more clearly in FIG. 1B. Drip portion 18 has a gradual transition surface 20, preferably curved, and is configured with an extended lower lip portion 22 so as to guide exiting fluid sample into a fluid sample container 24 (described below). Preferably, a fluid reservoir 26 is formed proximate to the fluid inlet orifice 14 for receiving fluid sample prior to introducing the fluid sample to elongated narrow tube 12.

Referring again to FIG. 1A, the temperature of fluid sample passing through elongated narrow tube 12 is maintained by a heat exchange medium or insulating jacket 28 wrapped about elongated narrow tube 12. Insulating jacket 28 is preferably a circulating liquid bath arranged about the perimeter of the elongated narrow tube 12 along its entire length. A liquid inlet port 30 and liquid outlet port 32 are provided in the insulating jacket 28 for circulating liquid having the appropriate temperature thereby maintaining the temperature of the fluid sample virtually constant during sampling. Circulating bath 28 provides a heat exchange medium along the length of elongated narrow tube 12. Knowing the density of the liquid and the capillary constant, the viscosity is calculated with average relative deviation of less than 2% over viscosities ranging from 0.41–103 cp.

Referring again to FIG. 1A, a fluid sample container 24, such as a beaker, is positioned beneath elongated narrow tube 12 for receiving fluid sample exiting the drip portion 18 of elongated narrow tube 12. Fluid sample container 24 is supported on a serial interfaced, preferably digital, balance 34, such as one made by Mettler Toledo, Model Number PB302 of Columbus, Ohio. Digital balance 34 is arranged so that fluid sample container 24 receives fluid sample passing through elongated narrow tube 12 and exiting fluid outlet orifice 16 without creating turbulence. As fluid sample 23 enters fluid sample container 24, digital balance 34 generates a digital output signal corresponding to the weight of the fluid sample container 24 containing fluid sample 23. Thus, digital balance 34 provides a plurality of weights of fluid sample container 24 containing predetermined amounts of fluid being tested.

Referring again to FIG. 1A, serially connected to digital balance 34 is processor or computer 36 for processing the generated digital output signals corresponding to the plurality of weights of fluid sample container 24 containing various amounts of fluid. Skilled artisans will appreciate that computer 36 contains a computer readable program for enabling the computer 36 to receive the digital signals representing the plurality of weights and then interpreting the digital signals as viscosity of the fluid sample being tested.

Several factors are considered important in the development and effectiveness of the apparatus 10 of the invention. Sample volume was to be minimized and kept below 15 mL. To allow for adequate measurement time, the volume of sample contained in the elongated narrow tube 12 should be no more than 10% of the total sample volume. Further, entrance flow effect and Reynolds number, Re, should be minimized so as to allow interpretation of flow rate by the Poiseuille equation. Moreover, change in pressure head at the fluid inlet orifice 14 of elongated narrow tube 12 should be kept within acceptable limits (ca. 2%) with respect to loss of sample. Still further, the inner diameter ID of elongated narrow tube 12 should preferably be kept greater than 100 times the maximum particle size present in the fluid sample. Additionally, the ID of elongated narrow tube 12 should be kept greater than the minimum required to allow the liquid to initiate flow due to its own pressure head (against the back pressure due to surface tension). Finally, the effects of surface tension should be minimized at the fluid outlet orifice 16 so as not to require the introduction of a surface tension correction.

The invention will be further illustrated via the below examples.

EXAMPLE 1

The diameter of the pigment particles present in the inks is nominally 10 nm while that of the largest particles is ca. 100 nm, implying that ID >10.0 µm in order to ensure that ID is at least 100 times the size of the largest particles present in the fluid sample.

In order to overcome surface tension in elongated narrow tube 12 and ensure that the fluid sample will flow through the elongated narrow tube 12 upon introduction to the fluid reservoir 26, the Laplace pressure must be overcome. According to basic principles, Laplace pressure is defined by the equation $$p_{Laplace} = \frac{4\gamma}{D},$$

where $\gamma$ is the surface tension of the liquid. The pressure head provided by a sample of height h is $P_{sample}=\rho gh$. So, $$\rho gh > \frac{4\gamma}{D} \qquad \text{Equation 1}$$

Taking (only somewhat arbitrarily) the sample reservoir height h to be 2 cm and the density $\rho=1.0$ gcm$^{-3}$, Equation 1 gives D$\geq$0.14 cm, which overrides that specified by the particle size restriction.

Low Re ensures that the flow remains laminar, a condition met in pipe flow when Re<2000. This results in $$D \leq 4\left(\frac{\mu}{\rho}\right)^{2/3},$$

which is satisfied for water when D$\leq$0.185 cm. This condition is also superceded by the minimum diameter required by surface tension considerations.

Moreover, to allow for adequate measurement time, the volume of the fluid sample in elongated narrow tube 12 at any given time must be restricted to less than 0.1 of the total sample volume. This is given by the following relation between length L and diameter D $$10\frac{\pi D^2 L}{4} \leq 15 \text{ cm}^3 \qquad \text{Equation 2}$$

resulting in L$\leq$100 cm with D=0.14 cm as required by the Laplace pressure consideration.

The entrance length is the distance within the elongated narrow tube 12 over which the fluid travels before the velocity field reaches steady state in the Lagrangian sense. Entrance length and flow rate can be related through the Reynolds number by $$L_e \approx D\frac{\text{Re}}{30},$$

where $$\text{Re} = \frac{\rho \bar{v} D}{\mu}.$$

The mean velocity $$\bar{v} = \frac{4Q}{\pi D^2},$$

Where Q is the volumetric flow rate, so $$L_e = \frac{\rho 4Q}{30\mu\pi}.$$

In order to ensure that fully developed flow dominates the flow rate and thus the measurement, we require that L >>$L_e$ or, $$L \geq 10 \cdot L_e = \frac{4}{3\pi} \frac{\rho Q}{\mu} \qquad \text{Equation 3}$$

If Re <2000 so that the flow remains laminar, then the volumetric flow rate Q is obtained through the Poiseuille equation, for which the pressure head is due to the sample, $$\frac{\rho g(L+h)}{L} = \frac{128\mu Q}{\pi D^4},$$

where g is the gravitational acceleration. Since h<<L, this leads to $$L \approx \frac{1}{100}\left(\frac{\rho}{\mu}\right)^2 g D^4 \qquad \text{Equation 4}$$

EXAMPLE 2

Using water as an example, as it has both viscosity and density close to those of ink jet printing inks, Equation 4 and D as required by surface tension considerations, the capillary length is given by $$L \approx \frac{1}{100}\left(\frac{1.0 g \text{ cm}^{-3}}{0.01 g \text{ cm}^{-1}\text{s}^{-1}}\right)^2 g(0.14 \text{ cm})^4 = 38 \text{ cm}$$

At the exit, a gently flared opening would ensure that at the lower free surface of the fluid, the Laplace pressure would be that due to the larger diameter and not represent a significant correction.

The fluid reservoir 26 diameter was determined in order to keep the change in pressure head with changing sample volume within an acceptable range. As pressure drop and flow rate (from which viscosity is to be calculated) are linearly related, change in sample height in the reservoir relative to L is reflected in the same relative change in volumetric flow rate. In order to measure viscosity within the acceptable error of ca. 2%, the change in sample volume height Δh must then remain below 1 cm.

The diameter of the fluid reservoir 26 must then hold the volume of liquid required to complete a measurement in measurement time t. This implies $$D_{res} = \left(\frac{4Qt}{\pi \Delta h}\right)^{\frac{1}{2}}.$$

Again taking water as an example, $$Q = \frac{(1.0 g \text{ cm}^{-3})(980 \text{ cms}^{-2})\pi(0.14 \text{ cm})^4}{128(0.01 g \text{ cm}^{-1}\text{s}^{-1})} \approx 1 \text{ cm}^3\text{s}^{-1}$$

which gives a reservoir diameter of $$D_{res} = \left(\frac{4(1.0 \text{ cm}^3\text{s}^{-1}(10 \text{ s}))}{\pi(1.0 \text{ cm})}\right)^{\frac{1}{2}} = 3.6 \text{ cm}.$$

The apparatus or viscometer 10 of the invention was manufactured according to the previously calculated specification, i.e. capillary length L =40 cm, inner diameter as close as available to 0.14 cm which was ID ≈0.1 cm, and reservoir diameter of 4 cm. The ID was specified due to the ability of the pressure head in the sample reservoir to overcome the Laplace pressure. Decreasing this value, while remaining safely above the minimum of 10 $\mu$m, would serve only to decrease the entrance length and Reynolds number, but possibly require assistance in initiating flow. The water jacket diameter was taken to be that of the sample reservoir.

Mass flow rate was detected by using an analytical balance, Mettler model PB302, which has serial computer interface, fast response time (≈0.1s), and can be operated in a continuous output mode. Mass values are read from the balance at ca 1 second intervals and flow rates are determined by total mass of efflux and time efflux.

Viscosity is calculated straightforwardly from mass flow rate q and density according to the Poiseuille equation:

$$\mu = \frac{\rho^2 g(h+L)\pi D^4}{128 L q} = K\frac{\rho^2}{q} \qquad \text{Equation 5}$$

where all constants save density have been lumped into a single constant K, descriptive of the particular capillary.

Calibration of the capillary was performed by measuring the mass flow rates of various pure fluids of known viscosity and density. The fluids used spanned a viscosity range of 0.405–103 mPas and a range of surface tension of 24–72 dynes/cm. As it was desired to calculate K with constant relative error, a weighted least squares routine was used with the fluid viscosity as the weighting factor. Since $$\chi^2 = \sum\left(\frac{\mu - K\frac{\rho^2}{q}}{\mu}\right)^2,$$

minimization of $\chi_{102}^2$ with respect to K results in:

$$K = \frac{\sum\left(\frac{\rho^2}{q\mu}\right)}{\sum\left(\frac{\rho^2}{q\mu}\right)^2} \qquad \text{Equation 6}$$

Figure 2:
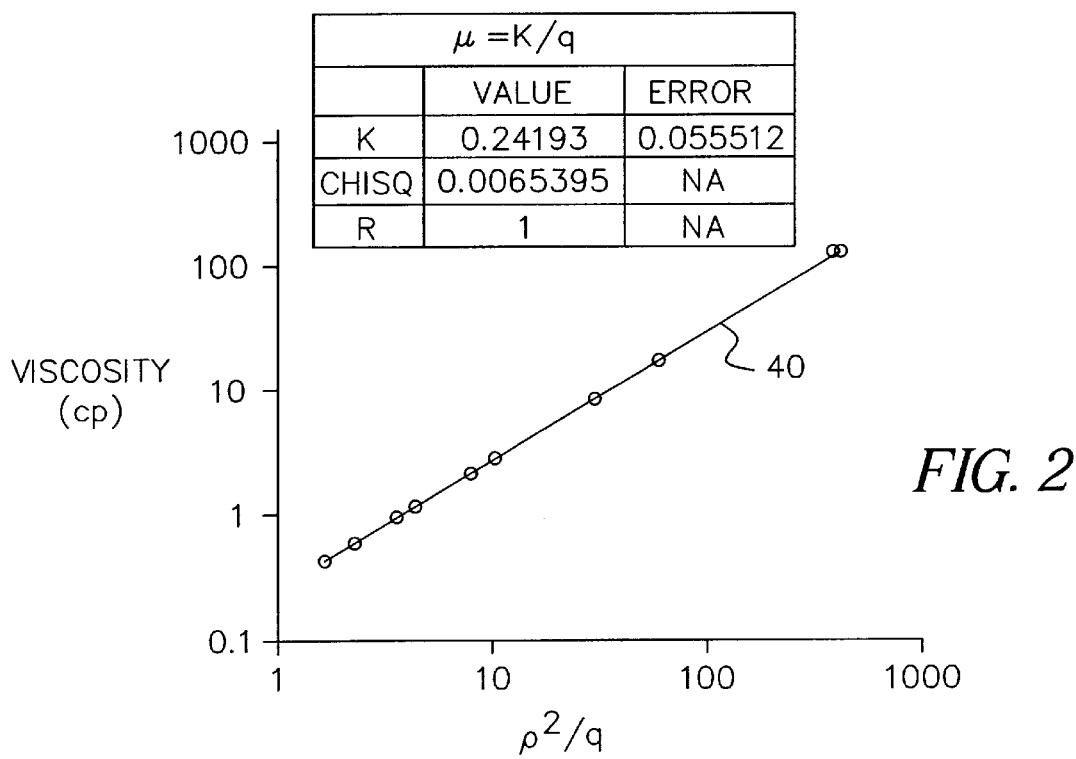
FIG. 2 is a capillary viscometer calibration curve of the invention.

Referring to FIG. 2, the calibration plot 40 shows a good fit was obtained from the flow rate data of the complete range of fluids tested, with capillary constant K=0.242. No correction was necessary to account for surface tension differences. The data are listed in Table 1.

TABLE 1

| Sample | Density (g/mL) | Viscosity (mPas) | Surface Tension (dyne/cm) | q (g/s) |
|---|---|---|---|---|
| 2-butanone | 0.79940 | 0.40500 | 24.000 | 0.38481 |
| 2-butanone | 0.79940 | 0.40500 | 25.000 | 0.38099 |
| Toluene | 0.86470 | 0.56000 | 28.000 | 0.31790 |
| Toluene | 0.86470 | 0.56000 | 28.000 | 0.31790 |
| Water | 0.99700 | 0.89000 | 72.000 | 0.27500 |
| Water | 0.99700 | 0.89000 | 72.000 | 0.27050 |
| Methanol | 0.78720 | 0.54400 | 24.500 | 0.26805 |
| Ethanol | 0.78730 | 1.0740 | 24.000 | 0.13967 |
| Ethanol | 0.78730 | 1.0740 | 24.000 | 0.13911 |
| 1-propanol | 0.80200 | 1.9450 | 24.000 | 0.080500 |
| 1-propanol | 0.80200 | 1.9450 | 24.000 | 0.080400 |
| 1-butanol | 0.80610 | 2.5440 | 24.000 | 0.062900 |
| 1-butanol | 0.80610 | 2.5440 | 24.000 | 0.062400 |
| 1-octanol | 0.82700 | 7.2880 | 27.500 | 0.022140 |

TABLE 1-continued

| Sample | Density (g/mL) | Viscosity (mPas) | Surface Tension (dyne/cm) | q (g/s) |
|---|---|---|---|---|
| 1-octanol | 0.82700 | 7.2880 | 27.500 | 0.022090 |
| N10 | 0.86090 | 14.870 | | 0.012379 |
| N10 | 0.86090 | 14.870 | | 0.012323 |
| S60 | 0.86210 | 102.50 | | 0.0018199 |
| S60 | 0.86210 | 102.50 | | 0.0017150 |

Figure 3:
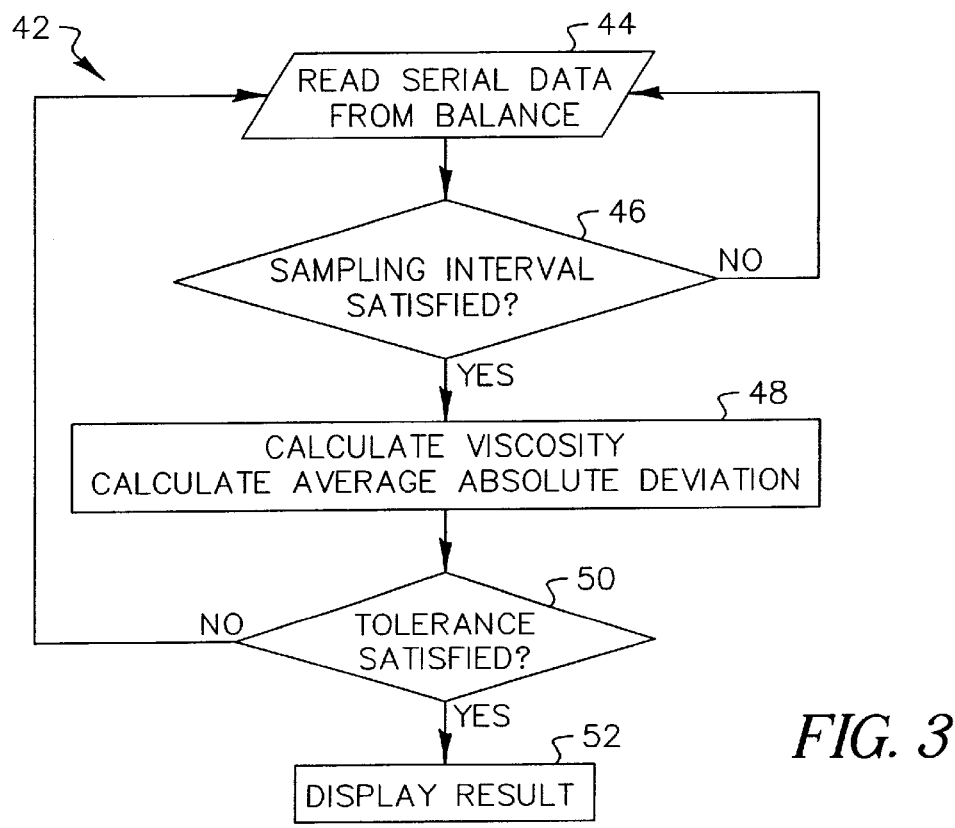
FIG. 3 is a flow chart of the viscosity measurement process.

Referring to FIG. 3, the general process 42 of the viscosity measurement is illustrated. In operation, after connecting the heat exchange medium or insulating jacket 28 to a controlled temperature bath via the liquid inlet and outlet ports 30 and 32, respectively (as shown clearly in FIG. 1A), the apparatus or viscometer 10 should be clamped in such a manner that the efflux is centered on the digital balance 34. The distance between the apparatus or viscometer 10 and the fluid sample container 24 on the digital balance 34 should be kept to a minimum to eliminate splashing.

Once serial communication has been established between the computer 36 and digital balance 34, the viscometer application can be started. Upon startup, the current calibraton constants will be displayed. These values are stored in an ASCII text file named calfile.txt, which must be in the same directory as the program itself. Secondly, the operator will be prompted for a log file name, to which are appended the sample name, time, mass, density, and viscosity for each sample measured. Files selected as log files are always opened in append mode, so the same log file can be selected between sessions without loss of data.

Before a measurement is made, further mention should be made of the calibration constant file, calfile.txt, which contains the following (in order):

1. offset (cp)—This constant should be 0 according to Equation 5, but is provided should an unforeseen correction be necessary.
2. K cpg$^{-1}$s
3. density (gmL$^{-1}$)
4. tolerance—The tolerance is the value of average relative deviation which must be reached before a viscosity measurement is automatically terminated. Mass is sampled at ca 1 second intervals and viscosity determined by K, total mass of efflux, and efflux time as indicated in Equation 5. The average relative deviation is calculated as $$ADev = \frac{1}{N}\sum_{1}^{N}\left|\frac{\mu - \frac{1}{N}\sum_{1}^{N}\mu_j}{\mu_i}\right| \text{ where currently, } N = 10,$$

so that the tolerance test applies to the most recent 10 values. Once the average deviation falls below that specified in calfile.txt, the measurement terminates and the values are displayed.

5. Capillary ID (cm)—This is only used in estimation of the shear rate, where the average shear rate of a Newtonian fluid in Poiseuille flow is $$\langle \gamma \rangle = \frac{8Q}{3\pi R^3}.$$

To change any of these values, select Set Calibration Constants from the Calibration menu.

To start a measurement, select New from the Measurement menu. The first time New is selected the operator will be prompted for a serial port which will subsequently be tested. The operator will then be prompted for a sample name. The sample name should not include white space as the output file name for the individual sample is automatically generated from the sample name, i.e. sampleName_viscosity_data.txt and placed in the directory specified with the log file. Once the sample name has been entered, a message box will appear indicating that the measurement will begin upon selecting OK.

The sample is then introduced into the fluid reservoir 26 and once it is flowing steadily through elongated narrow tube 12, select OK to begin the measurement process 42 (FIG. 3). According to FIG. 3, as the fluid sample flows through elongated narrow tube 12 and deposits into fluid sample container 24 (Step 44), sequential weights are determined by balance 34 and read by computer 36. Step 44 is repeated (Step 46) until a predetermined sampling interval has been achieved. Once the sampling interval has been achieved, both viscosity and the average absolute deviation are recalculated (Step 48). Steps 44 through 48 are repeated until a preset average absolute deviation, i.e., tolerance, has been achieved. Once this tolerance condition has been satisfied Step 50, the final viscosity result will be displayed 52.

Once the measurement is accepted according to the value for tolerance, a dialog box will be displayed containing sample name, time, mass, density, viscosity, and approximate shear rate. At the lower right of the dialog box will be a button labeled "Add to Standards Data." If the actual values of viscosity and density for the fluid sample are known, one can add the last measurement to the viscosity standards data by selecting this button. After selecting "Add to Standards Data," the operator will be prompted for the correct values of density and viscosity.

After at least one measurement has been saved as a standard, the capillary constant can be calculated by selecting Calculate Constant from the Calibration menu. The new value for K will be displayed, with which the operator may then choose to update the calibration file.

The invention has been described with reference to a preferred embodiment. However, it will be appreciated that variations and modifications can be effected by a person of ordinary skill in the art without departing from the scope of the invention.

What is claimed is:

1. An apparatus for determining viscosity of a fluid, comprising:
    an elongated tube for sampling a fluid, said elongated tube having a fluid inlet orifice and a fluid outlet orifice and wherein said elongated tube has a length L determined by the relations
    L≈1/100(ρ/μ)$^2$gD$^4$, wherein:
    ρ is the fluid density;
    μ is the fluid viscosity;
    g is the acceleration due to gravity; and,
    D is the diameter of the tube;
    a fluid sample container arranged beneath said elongated tube for receiving a sample of fluid exiting said fluid outlet orifice of said elongated tube;
    means for supporting said fluid sample container, said means for supporting providing a plurality of weights of said sample of fluid; and,
    a computer operably connected to said means for supporting, said computer comprising a computer readable program for enabling said computer to receive digital signals representing said plurality of weights from said means for supporting and then interpreting said digital signals as a measure of viscosity of said sample of fluid.

2. The apparatus recited in claim 1 wherein a drip portion extends beyond said fluid outlet orifice of said elongated tube, said drip portion being configured with an extended lower lip portion so as to guide exiting fluid sample into said fluid sample container.

3. The apparatus recited in claim 2 wherein said extended lower lip portion of said drip portion is directed substantially downwardly into said fluid sample container.

4. The apparatus recited in claim 2 wherein a gradual surface transition is formed between said elongated tube and said drip portion.

5. The apparatus recited in claim 4 wherein said gradual surface transition is curved shaped.

6. The apparatus recited in claim 1 wherein an insulating jacket is arranged about said elongated tube for temperature control of said fluid.

7. The apparatus recited in claim 6 wherein said insulating jacket comprises a heat exchange medium along the surface of said elongated tube.

8. The apparatus recited in claim 7 wherein said heat exchange medium is a circulating liquid bath.

9. The apparatus recited in claim 1 wherein fluid is introduced to said elongated tube from a fluid reservoir formed in an upper end portion of said elongated tube.

10. The apparatus recited in claim 1 wherein said elongated tube has a length (L) of 40 cm and an inner diameter of about 0.14 cm.

11. The apparatus recited in claim 10 wherein said inner diameter of said elongated tube is at least two orders of magnitude greater than the largest particle size in said sample of fluid.

12. The apparatus recited in claim 10 wherein said elongated tube has an inner diameter configured to accommodate particle sizes in said sample of fluid.

13. A method of measuring viscosity of a fluid, comprising the steps of:

introducing a fluid sample having a temperature (t) into an elongated tube;

controlling said temperature (t) of said fluid sample in said elongated tube;

determining a plurality of weights of said fluid sample passing through said elongated tube and collected from said elongated tube, wherein said step of determining a plurality of weights further comprising the step of using a variable sampling interval for sampling said plurality of weights and for determining a duration of said variable sampling interval; and, converting said plurality of weights of said fluid sample into a measure of viscosity of said fluid sample.

14. The method recited in claim 13 wherein said step of converting comprises the step of determining mass flow rate of said fluid sample and converting said mass flow rate into viscosity.

15. The method recited in claim 13 wherein said step of controlling the temperature of said elongated tube comprises the step of applying a heat exchange medium about the length of said elongated tube.

16. The method recited in claim 13 further comprising, after the step of converting, the step of calculating a standard deviation of said viscosity.

17. The method recited in claim 16 wherein said step of calculating said standard deviation further includes the step of using said standard deviation as an acceptance criteria.

* * * * *